(12) United States Patent
Oppelaar

(10) Patent No.: US 7,705,213 B2
(45) Date of Patent: Apr. 27, 2010

(54) BEAN LINE RS08051272

(75) Inventor: Arie Oppelaar, Ochten (NL)

(73) Assignee: Seminis Vegetable Seeds, Inc., Woodland, CA (US)

( * ) Notice: Subject to any disclaimer, the term of this patent is extended or adjusted under 35 U.S.C. 154(b) by 130 days.

(21) Appl. No.: 12/099,029

(22) Filed: Apr. 7, 2008

(65) Prior Publication Data

US 2009/0255007 A1    Oct. 8, 2009

(51) Int. Cl.
- *A01H 5/00* (2006.01)
- *A01H 5/10* (2006.01)
- *A01H 1/00* (2006.01)
- *C12N 5/04* (2006.01)
- *C12N 15/82* (2006.01)

(52) U.S. Cl. .................. 800/313; 800/260; 800/278; 800/298; 435/410; 435/420; 435/430; 435/421

(58) Field of Classification Search .................. None
See application file for complete search history.

(56) References Cited

U.S. PATENT DOCUMENTS 6,924,419 B2 *   8/2005  Magnuson ............... 800/313
2008/0172753 A1   7/2008  Kotch et al. ............. 800/313

OTHER PUBLICATIONS

Application for Plant Breeders Rights No. BON 1720 for Bean variety RX 0851272, The Netherlands dated Apr. 13, 2007.
Application No. 2008/0175 for Community Plant Variety Right for Bean variety *Pisum sativum* L. RX 0851272, European Union, dated Jan. 23, 2008.
PVP Certificate for Garden Bean Variety RS 1260, dated May 3, 2007.

* cited by examiner

*Primary Examiner*—Stuart F. Baum
(74) *Attorney, Agent, or Firm*—Alissa M. Eagle, Esq.; Sonnenschein Nath & Rosenthal LLP

(57) ABSTRACT

The invention provides seed and plants of the bean line designated RS08051272. The invention thus relates to the plants, seeds and tissue cultures of bean line RS08051272, and to methods for producing a bean plant produced by crossing a plant of bean line RS08051272 with itself or with another bean plant, such as a plant of another line. The invention further relates to seeds and plants produced by such crossing. The invention further relates to parts of a plant of bean line RS08051272, including the pods and gametes of such plants.

23 Claims, No Drawings

BEAN LINE RS08051272

FIELD OF THE INVENTION

The present invention relates to the field of plant breeding and, more specifically, to the development of bean line RS08051272.

BACKGROUND OF THE INVENTION

The goal of crop breeding is to combine various desirable traits in a single variety/hybrid. Such desirable traits may include greater yield, resistance to insects or pests, tolerance to heat and drought, better agronomic quality, higher nutritional value, growth rate and fruit or pod properties.

Breeding techniques take advantage of a plant's method of pollination. There are two general methods of pollination: a plant self-pollinates if pollen from one flower is transferred to the same or another flower of the same plant or plant variety. A plant cross-pollinates if pollen comes to it from a flower of a different plant variety.

Plants that have been self-pollinated and selected for type over many generations become homozygous at almost all gene loci and produce a uniform population of true breeding progeny, a homozygous plant. A cross between two such homozygous plants of different varieties produces a uniform population of hybrid plants that are heterozygous for many gene loci. Conversely, a cross of two plants each heterozygous at a number of loci produces a population of hybrid plants that differ genetically and are not uniform. The resulting non-uniformity makes performance unpredictable.

The development of uniform varieties requires the development of homozygous inbred plants, the crossing of these inbred plants, and the evaluation of the crosses. Pedigree breeding and recurrent selection are examples of breeding methods that have been used to develop inbred plants from breeding populations. Those breeding methods combine the genetic backgrounds from two or more plants or various other broad-based sources into breeding pools from which new lines are developed by selfing and selection of desired phenotypes. The new lines are evaluated to determine which of those have commercial potential.

One crop species which has been subject to such breeding programs and is of particular value is garden bean (*Phaseolus vulgaris* (snap)). Beans are annual, warm-season legumes. Garden beans, also known as green beans, snap beans, or pole beans, are grown primarily for their pods, which are harvested for consumption in their succulent form, whereas dry beans (*Phaseolus vulgaris* (dry)), lima beans (*Phaseolus limensis*), and soybeans (*Glycine max*) are usually grown for the seed itself. In addition, the bean leaf is occasionally used as a leaf vegetable, and the straw is used for fodder.

Garden beans are available in bush and pole varieties. Bush varieties form erect bushes 20-60 centimeters tall, while pole varieties form vines 2-3 meters long. The pods are typically 8-20 centimeters long, 1-1.5 centimeters wide, and either green, yellow, black or purple in color. Each pod generally contains 4-6 beans.

SUMMARY OF THE INVENTION

In one aspect, the present invention provides a bean plant of the bean line designated RS08051272. Also provided are bean plants having all the physiological and morphological characteristics of bean line RS08051272. Parts of the bean plant of the present invention are also provided, for example, including pollen, an ovule, a pod, and a cell of the plant.

The invention also concerns seed of bean line RS08051272. The bean seed of the invention may be provided as an essentially homogeneous population of bean seed of the line designated RS08051272. Essentially homogeneous populations of seed are generally free from substantial numbers of other seed. Therefore, seed of line RS08051272 may be defined as forming at least about 97% of the total seed, including at least about 98%, 99%, or more of the seed. The population of bean seed may be particularly defined as being essentially free from hybrid seed. The seed population may be separately grown to provide an essentially homogeneous population of bean plants designated RS08051272.

In another aspect of the invention, a plant of bean line RS08051272 comprising an added heritable trait is provided. The heritable trait may comprise a genetic locus that is, for example, a dominant or recessive allele. In one embodiment of the invention, a plant of bean line RS08051272 is defined as comprising a single locus conversion. In specific embodiments of the invention, an added genetic locus confers one or more traits such as, for example, herbicide tolerance, insect resistance, disease resistance, and modified carbohydrate metabolism. In further embodiments, the trait may be conferred by a naturally occurring gene introduced into the genome of the line by backcrossing, a natural or induced mutation, or a transgene introduced through genetic transformation techniques into the plant or a progenitor of any previous generation thereof. When introduced through transformation, a genetic locus may comprise one or more genes integrated at a single chromosomal location.

In another aspect of the invention, a tissue culture of regenerable cells of a plant of line RS08051272 is provided. The tissue culture will preferably be capable of regenerating plants capable of expressing all of the physiological and morphological characteristics of the line, and of regenerating plants having substantially the same genotype as other plants of the line. Examples of some of the physiological and morphological characteristics of the line RS08051272 include those traits set forth in the tables herein. The regenerable cells in such tissue cultures may be derived, for example, from embryos, meristems, cotyledons, pollen, leaves, anthers, roots, root tips, pistil, flower, seed and stalks. Still further, the present invention provides bean plants regenerated from a tissue culture of the invention, the plants having all the physiological and morphological characteristics of line RS08051272.

In yet another aspect of the invention, processes are provided for producing bean seeds, plants and pods, which processes generally comprise crossing a first parent bean plant with a second parent bean plant, wherein at least one of the first or second parent bean plants is a plant of the line designated RS08051272. These processes may be further exemplified as processes for preparing hybrid bean seed or plants, wherein a first bean plant is crossed with a second bean plant of a different, distinct line to provide a hybrid that has, as one of its parents, the bean plant line RS08051272. In these processes, crossing will result in the production of seed. The seed production occurs regardless of whether the seed is collected or not.

In one embodiment of the invention, the first step in "crossing" comprises planting seeds of a first and second parent bean plant, often in proximity so that pollination will occur for example, mediated by insect vectors. Alternatively, pollen can be transferred manually. Where the plant is self-pollinated, pollination may occur without the need for direct human intervention other than plant cultivation.

A second step may comprise cultivating or growing the seeds of first and second parent bean plants into plants that bear flowers. A third step may comprise preventing self-pollination of the plants, such as by emasculating the male portions of flowers, (i.e., treating or manipulating the flowers to produce an emasculated parent bean plant).

A fourth step for a hybrid cross may comprise cross-pollination between the first and second parent bean plants. Yet another step comprises harvesting the seeds from at least one of the parent bean plants. The harvested seed can be grown to produce a bean plant or hybrid bean plant.

The present invention also provides the bean seeds and plants produced by a process that comprises crossing a first parent bean plant with a second parent bean plant, wherein at least one of the first or second parent bean plants is a plant of the line designated RS08051272. In one embodiment of the invention, bean seed and plants produced by the process are first generation ($F_1$) hybrid bean seed and plants produced by crossing a plant in accordance with the invention with another, distinct plant. The present invention further contemplates plant parts of such an $F_1$ hybrid bean plant, and methods of use thereof. Therefore, certain exemplary embodiments of the invention provide an $F_1$ hybrid bean plant and seed thereof.

In still yet another aspect of the invention, the genetic complement of the bean plant line designated RS08051272 is provided. The phrase "genetic complement" is used to refer to the aggregate of nucleotide sequences, the expression of which sequences defines the phenotype of, in the present case, a bean plant, or a cell or tissue of that plant. A genetic complement thus represents the genetic makeup of a cell, tissue or plant, and a hybrid genetic complement represents the genetic make up of a hybrid cell, tissue or plant. The invention thus provides bean plant cells that have a genetic complement in accordance with the bean plant cells disclosed herein, and plants, seeds and plants containing such cells.

Plant genetic complements may be assessed by genetic marker profiles, and by the expression of phenotypic traits that are characteristic of the expression of the genetic complement, e.g., isozyme typing profiles. It is understood that line RS08051272 could be identified by any of the many well known techniques such as, for example, Simple Sequence Length Polymorphisms (SSLPs) (Williams et al., 1990), Randomly Amplified Polymorphic DNAs (RAPDs), DNA Amplification Fingerprinting (DAF), Sequence Characterized Amplified Regions (SCARs), Arbitrary Primed Polymerase Chain Reaction (AP-PCR), Amplified Fragment Length Polymorphisms (AFLPs) (EP 534 858, specifically incorporated herein by reference in its entirety), and Single Nucleotide Polymorphisms (SNPs) (Wang et al., 1998).

In still yet another aspect, the present invention provides hybrid genetic complements, as represented by bean plant cells, tissues, plants, and seeds, formed by the combination of a haploid genetic complement of a bean plant of the invention with a haploid genetic complement of a second bean plant, preferably, another, distinct bean plant. In another aspect, the present invention provides a bean plant regenerated from a tissue culture that comprises a hybrid genetic complement of this invention.

In still yet another aspect, the invention provides a plant of an inbred bean line that exhibits a combination of traits including early maturity, large pod length, resistance to Anthracnose—race Lambda, resistance to bean common mosaic virus (BCMV)-NL3 and resistance to bean common mosaic virus (BCMV)-NL4.

In certain embodiments, the trait may be defined as controlled by genetic means for the expression of the trait found in bean line RS08051272.

In still yet another aspect, the invention provides a method of determining the genotype of a plant of bean line RS08051272 comprising detecting in the genome of the plant at least a first polymorphism. The method may, in certain embodiments, comprise detecting a plurality of polymorphisms in the genome of the plant. The method may further comprise storing the results of the step of detecting the plurality of polymorphisms on a computer readable medium. The invention further provides a computer readable medium produced by such a method.

In still yet another aspect, the present invention provides a method of producing a plant derived from line RS08051272, the method comprising the steps of: (a) preparing a progeny plant derived from line RS08051272, wherein said preparing comprises crossing a plant of the line RS08051272 with a second plant; and (b) crossing the progeny plant with itself or a second plant to produce a seed of a progeny plant of a subsequent generation. In further embodiments, the method may additionally comprise: (c) growing a progeny plant of a subsequent generation from said seed of a progeny plant of a subsequent generation and crossing the progeny plant of a subsequent generation with itself or a second plant; and repeating the steps for an additional 3-10 generations to produce a plant derived from line RS08051272. The plant derived from line RS08051272 may be an inbred line, and the aforementioned repeated crossing steps may be defined as comprising sufficient inbreeding to produce the inbred line. In the method, it may be desirable to select particular plants resulting from step (c) for continued crossing according to steps (b) and (c). By selecting plants having one or more desirable traits, a plant derived from line RS08051272 is obtained which possesses some of the desirable traits of the line as well as potentially other selected traits.

In certain embodiments, the present invention provides a method of producing beans comprising: (a) obtaining a plant of bean line RS08051272, wherein the plant has been cultivated to maturity, and (b) collecting beans from the plant.

These and other features and advantages of this invention are described in, or are apparent from, the following detailed description of various exemplary embodiments of the devices and methods according to this invention.

DETAILED DESCRIPTION OF THE INVENTION

The invention provides methods and compositions relating to plants, seeds and derivatives of the bean line designated RS08051272. This line shows uniformity and stability within the limits of environmental influence for the traits described hereinafter. Bean line RS08051272 provides sufficient seed yield. By crossing with a distinct second plant, uniform F1 hybrid progeny can be obtained.

In specific embodiments, a plant of the invention exhibits a number of improved traits such as early maturity, large pod length, resistance to Anthracnose-race Lambda, resistance to bean common mosaic virus (BCMV)-NL3 and resistance to bean common mosaic virus (BCMV)-NL4.

A. Origin and Breeding History of RS08051272

RS08051272 was developed by pedigree selection from an initial cross between two breeding lines, 02D576-3 and 02D582-1.

Parent A, 02D576-3, an F5 breeding line from the original cross Cadillac×Sam, has a mid late maturing, high yielding, medium large pod diameter, 12 cm long pods, medium dark green pods, and is resistant to Halo Blight. (Cadillac: Seminis Vegetable Seeds, Inc.—US PVP 200400267).

Parent B, 02D582-1, an F5 breeding line from the original three-way cross Sam×(Prelude×RS1290), has an early maturing, large pod diameter, 12-14 cm long pods, light pod color, and is susceptible to Halo Blight. (Prelude and RS1290: Royal Sluis).

The initial cross was made in the greenhouse. After 7 generations of selfing and pedigree selection, a line was selected that combined the yield, medium large pod diameter, medium green pod color and a medium early maturity. The crossing and selections that led directly to RS08051272 can be summarized as follows:

| YEAR | SEASON | GENERATION | LOCATION | DESCRIPTION |
|---|---|---|---|---|
| Year 1 | Fall | A × B | Greenhouse Wageningen | Cross made |
| Year 2 | Spring | F1 | Greenhouse Wageningen | Increase, 700 seeds harvested in bulk 03/7294 |
| Year 2 | Summer | F2 | Field Wageningen | Planted all seeds from bulk 03/7294 in the field. 71 plants were selected for early maturity and pod uniformity and harvested as single plant selections. |
| Year 2 | Winter | F3 | Field Chile | All 71 single plant selections planted at 45 seeds per progeny. 1 line at stake 5806, originating from single plant #48 was selected for its early maturity and good plant habit and harvested in bulk. 20 seeds of this line was tested by pathology and found susceptible for Halo Blight. |
| Year 3 | Summer | F4 | Field Wageningen | Planted family 04/5806 in the selection field in Wageningen using 4 × 120 plants per family. Selected 18 single plants from the family at stake number 04D564, and harvested them separately. 10 seeds of each line were tested for resistance to Anthracnose race Lambda and found resistant. |
| Year 3 | Winter | F5 | Field Chile | Planted the 18 single plant selections at 45 seeds per progeny. The line at stake 4597, originating from single plant #5 was selected for its pod uniformity and early maturity. It has been harvested in bulk. |
| Year 4 | Summer | F6 | Field Wageningen | Planted seed from bulk 05/4597 in the selection field in Wageningen using 4 × 120 plants. Selected it for its horticultural characteristics and harvested 11 single plant selections at stake number 05D333. 10 seeds of each line were tested for Anthracnose race lambda and found resistant. |
| Year 4 | Fall | F7 | Greenhouse Wageningen | Planted 5 plants from each of the 11 F7 selections in the greenhouse in Wageningen for multiplication. Harvested 5 × 11 single plants. |
| Year 4 | Winter | F7 | Field Chile | Planted each of the 11 F7 selections in the field in Chile for progeny evaluation, observed that all of them had the same characteristic traits and were sufficiently uniform across; coded 05D333 as RS08051272. |
| Year 5 | Spring | F8 | Greenhouse Wageningen | Planted all 55 single plant selections from the greenhouse at 2 plants each in the greenhouse. 110 plants have been harvested as single plants and submitted to the foundation seed department. |
| Year 5 | Summer | F9 | Field Wageningen | Planted all 110 single plant selections in the foundation seed field at 45 plants per line. The lines proved to be stable and uniform for all described traits. No off types were found. The 110 lines were then bulked. |

Observations during three years confirmed that RS08051272 is uniform and stable for characteristics including but not limited to plant habit, maturity, pod type and other horticultural and agronomic characteristics. As is true with other garden beans, a very small percentage of mutations for flat pods or string may occur during repeated multiplication. RS08051272 is within the commercially acceptable limits of 0.1% (for flat pods) and 0.01% (for string) for this type of mutation. No genetic variants have been observed or are expected to occur in future generations of RS08051272.

B. Physiological and Morphological Characteristics of Bean Line RS08051272

In accordance with one aspect of the present invention, there is provided a plant having the physiological and morphological characteristics of bean line RS08051272. A description of the physiological and morphological characteristics of bean line RS08051272 is presented in Table 1.

TABLE 1

Physiological and Morphological Characteristics of Line RS08051272

| CHARACTERISTIC | RS08051272 |
|---|---|
| Type | Garden |
| Market Maturity | |
| Days to Edible Pods | 72 |
| Number of Days Earlier than the Comparison Variety | 4 Days Earlier than Cadillac |
| Plant | |
| Habit | Determinate |
| Height in cm | 35 cm |
| Number of Centimeters Shorter than the Comparison Variety | 5 cm Shorter than Cadillac |
| Plant spread (width) in centimeters | 40 cm |
| Comparison Variety that is the Same Width as the Applicant Variety | Cadillac |
| Pod Position | High |
| Bush Form | High Bush Form |
| Growth Type | Dwarf |
| Dwarf Beans | |
| Plant: type | Non-trailing |
| Plant: height | Medium |
| Leaves | |
| Surface | Dull |
| Size | Medium |
| Color | Dark Green |
| Leaf | |
| Intensity of Green Color | Dark |
| Rugosity | Medium |
| Terminal Leaflet | |
| Size | Medium |
| Shape | Rhombic |
| Length of Tip | Long |
| Dwarf beans | |
| Inflorescences: position (at full flowering) | Intermediate |
| Flower | |
| Size of Bracts | Small |
| Color of Standard | White |
| Color of Keel | White |
| Days to 50% Bloom | 51 |
| Pods | |
| Exterior Color (fresh) | Medium Green |
| Processed Pods (exterior color) | Light |

TABLE 1-continued

Physiological and Morphological Characteristics of Line RS08051272

| CHARACTERISTIC | RS08051272 |
|---|---|
| Dry Pod Color | Buckskin |
| Pod Length (excluding beak) | Medium |
| Width | Narrow |
| Thickness | Medium |
| Ratio Thickness/Width | Medium |
| Shape in Cross Section | Circular |
| Crease back | Absent |
| Pubescence | Sparse |
| Constriction at Dry Seed Stage | Absent or Very Weak |
| Spur Length | 10-12 mm |
| Fiber | Sparse |
| Number of Seeds per Pod | 7 |
| Stringiness of Ventral Suture | Absent |
| Seed Development | Medium |
| Machine harvest | Adapted |
| Percent Sieve Size Distribution at Optimum Maturity for Non-Flat Pods | |
| 7.34 to 8.34 mm | 10% |
| 8.34 to 9.53 mm | 40% |
| 9.53 to 10.72 mm | 50% |
| 3 Sieve | 12 cm length × 9 mm width |
| 4 Sieve | 12.5 cm length × 10 mm width |
| 5 Sieve | 13 cm length × 10.5 mm width |
| Ground color | Green |
| Intensity of Ground Color | Medium |
| Presence of Secondary Color | Absent |
| Degree of Curvature | Weak |
| Shape of Curvature | Concave |
| Shape of Distal Part | Truncate |
| Length of Beak | Medium |
| Curvature of Beak | Weak |
| Texture of Surface | Smooth or Slightly |
| Seed | |
| Weight | Medium |
| Seed Coat Luster | Dull |
| Seed Coat | Monochrome |
| Number of Colors | One |
| Color: Main/Primary color (largest area) | White |
| Coat Pattern | Solid |
| Veining | Medium |
| Hilar Ring | Absent |
| Shape and Size: Hilum View | Oval |
| Shape and Size: Side View | Oval to Oblong |
| Shape in Longitudinal Section | Elliptic |
| Shape in Cross Section | Medium Elliptic |
| Width in Cross Section | Medium |
| Length | Medium |
| Shape and Size: gm/100 Seeds | 26 gms |
| Shape and Size: gm/100 Seeds Lighter Than the Comparison Variety | 8 gms |
| Time of Flowering (50% of the Plants with at Least One Flower) | Early |
| Disease Resistance | |
| Anthracnose (*Colletotrichum lindemuthianum*) - Race Lambda | Resistance/Present |
| Common Blight (*Xanthomonas campestris*) | Absent |
| Halo Blight (*Psudomonas syringae* pv *Phaseolicola*)-Race 2 | Susceptible/Absent |
| Bean Common Mosaic Virus (BCMV) - NL3 | Resistant |
| Bean Common Mosaic Virus (BCMV) - NL4 | Resistant |
| Type of resistance to Bean Common Mosaic Virus (BCMV) | Mosaic Development Absent, Blackroot Development Present |

*These are typical values. Values may vary due to environment. Other values that are substantially equivalent are within the scope of the invention.

Line RS08051272 has been self-pollinated and planted for a number of generations to produce the homozygosity and phenotypic stability to make this line useful in commercial seed production. No variant traits have been observed or are expected for this line.

Bean line RS08051272, being substantially homozygous, can be reproduced by planting seeds of the line, growing the resulting bean plant under self-pollinating or sib-pollinating conditions and harvesting the resulting seeds using techniques familiar to one of skill in the art.

C. Breeding Bean Line RS08051272

One aspect of the current invention concerns methods for crossing the bean line RS08051272 with itself or a second plant and the seeds and plants produced by such methods. These methods can be used for propagation of line RS08051272, or can be used to produce hybrid bean seeds and the plants grown therefrom. Hybrid seeds are produced by crossing line RS08051272 with second bean parent line.

The development of new varieties using one or more starting varieties is well known in the art. In accordance with the invention, novel varieties may be created by crossing line RS08051272 followed by multiple generations of breeding according to such well known methods. New varieties may be created by crossing with any second plant. In selecting such a second plant to cross for the purpose of developing novel lines, it may be desired to choose those plants which either themselves exhibit one or more selected desirable characteristics or which exhibit the desired characteristic(s) in progeny. Once initial crosses have been made, inbreeding and selection take place to produce new varieties. For development of a uniform line, often five or more generations of selfing and selection are involved.

Uniform lines of new varieties may also be developed by way of double-haploids. This technique allows the creation of true breeding lines without the need for multiple generations of selfing and selection. In this manner, true breeding lines can be produced in as little as one generation. Haploid embryos may be produced from microspores, pollen, anther cultures, or ovary cultures. The haploid embryos may then be doubled autonomously, or by chemical treatments (e.g. colchicine treatment). Alternatively, haploid embryos may be grown into haploid plants and treated to induce chromosome doubling. In either case, fertile homozygous plants are obtained. In accordance with the invention, any of such techniques may be used in connection with line RS08051272 and progeny thereof to achieve a homozygous line.

New varieties may be created, for example, by crossing line RS08051272 with any second plant and selection of progeny in various generations and/or by doubled haploid technology. In choosing a second plant to cross for the purpose of developing novel lines, it may be desired to choose those plants which either themselves exhibit one or more selected desirable characteristics or which exhibit the desired characteristic(s) in progeny. After one or more lines are crossed, true-breeding lines may be developed.

Backcrossing can also be used to improve an inbred plant. Backcrossing transfers a specific desirable trait from one inbred or non-inbred source to an inbred that lacks that trait. This can be accomplished, for example, by first crossing a superior inbred (A) (recurrent parent) to a donor inbred (non-recurrent parent), which carries the appropriate locus or loci for the trait in question. The progeny of this cross are then mated back to the superior recurrent parent (A) followed by selection in the resultant progeny for the desired trait to be transferred from the non-recurrent parent. After five or more backcross generations with selection for the desired trait, the progeny are heterozygous for loci controlling the characteristic being transferred, but are like the superior parent for most or almost all other loci. The last backcross generation would be selfed to give pure breeding progeny for the trait being transferred.

The line of the present invention is particularly well suited for the development of new lines based on the elite nature of the genetic background of the line. In selecting a second plant to cross with RS08051272 for the purpose of developing novel bean lines, it will typically be preferred to choose those plants which either themselves exhibit one or more selected desirable characteristics or which exhibit the desired characteristic(s) when in hybrid combination. Examples of desirable characteristics may include, for example, seed yield, seed size, seed shape, seed uniformity, pod size, pod shape, pod color, pod uniformity, early maturity, disease resistance, herbicide tolerance, seedling vigor, adaptability for soil conditions, adaptability for climate conditions, and uniform plant height.

D. Performance Characteristics

Performance characteristics of the line RS08051272, were the subject of an objective analysis of the performance traits of the line relative to other lines. Results from the analysis are presented below in Tables 2-4.

TABLE 2

Trial 1: Guerbigny, France.
Plot size: 120 plants; harvested 30 plants per plot per harvest.

| Variety | Plot# | Maturity (Days from sowing date) | Pod length sieve 4 (cm) |
|---|---|---|---|
| Cadillac | 12257 | 74 | 11.2 |
| Cadillac | 12641 | 75 | 11.3 |
| RS08051272 | 12271 | 68 | 12.8 |
| RS08051272 | 12657 | 71 | 12.7 |

TABLE 3

Trial 2: Guerbigny, France.
Plot size: 120 plants; harvested 30 per plot per harvest date.

| Variety | Plot# | Maturity (Days from sowing date) | Pod length sieve 4 (cm) |
|---|---|---|---|
| Cadillac | 22257 | 72 | 11.4 |
| Cadillac | 25312 | 74 | 11.3 |
| Cadillac | 22628 | 73 | 11.5 |
| Cadillac | 25651 | 75 | 11.4 |
| RS08051272 | 22271 | 69 | 12.9 |
| RS08051272 | 25356 | 71 | 13.2 |
| RS08051272 | 22668 | 68 | 12.8 |
| RS08051272 | 25702 | 70 | 12.9 |

TABLE 4

Trial 3: Guerbigny France.
Plot size: 120 plants; harvested 30 per plot per harvest date.

| Variety | Plot# | Maturity | Pod length sieve 4 (cm) |
|---|---|---|---|
| Cadillac | 32271 | 74 | 11.3 |
| Cadillac | 32649 | 76 | 11.3 |
| RS08051272 | 32336 | 69 | 12.5 |
| RS08051272 | 32756 | 72 | 12.4 |

Analysis of trial results across trials can be summarized as follows:

The maturity mean value is 71.93 days across varieties, 74.13 days for Cadillac (Sd 1.25) and 69.75 days for RS08051272 (Sd. 1.31). The standard error of difference is 1.81, with a t-value of (74.13-69.75)/1.81=2.42. This t-value indicates that the varieties do have a significant difference in maturity at >95% probability.

The pod length across sieve sizes has a mean value of 12.06 cm across varieties, 11.34 cm for Cadillac (Sd 0.09) and 12.78 for RS08051272 (Sd 0.25). The standard error of difference is 0.266 with a t-value of (12.78-11.34)/0.27=5.33. This t-value indicates that both varieties are different for pod length with a high (>99%) probability.

E. Further Embodiments of the Invention

When the term bean line RS08051272 is used in the context of the present invention, this also includes plants modified to include at least a first desired heritable trait. Such plants may, in one embodiment, be developed by a plant breeding technique called backcrossing, wherein essentially all of the desired morphological and physiological characteristics of a variety are recovered in addition to a genetic locus transferred into the plant via the backcrossing technique. The term single locus converted plant as used herein refers to those bean plants which are developed by a plant breeding technique called backcrossing, wherein essentially all of the desired morphological and physiological characteristics of a variety are recovered in addition to the single locus transferred into the variety via the backcrossing technique.

Backcrossing methods can be used with the present invention to improve or introduce a characteristic into the present variety. The parental bean plant which contributes the locus for the desired characteristic is termed the nonrecurrent or donor parent. This terminology refers to the fact that the nonrecurrent parent is used one time in the backcross protocol and therefore does not recur. The parental bean plant to which the locus or loci from the nonrecurrent parent are transferred is known as the recurrent parent as it is used for several rounds in the backcrossing protocol.

In a typical backcross protocol, the original variety of interest (recurrent parent) is crossed to a second variety (nonrecurrent parent) that carries the single locus of interest to be transferred. The resulting progeny from this cross are then crossed again to the recurrent parent and the process is repeated until a bean plant is obtained wherein essentially all of the desired morphological and physiological characteristics of the recurrent parent are recovered in the converted plant, in addition to the single transferred locus from the nonrecurrent parent.

The selection of a suitable recurrent parent is an important step for a successful backcrossing procedure. The goal of a backcross protocol is to alter or substitute a single trait or characteristic in the original variety. To accomplish this, a single locus of the recurrent variety is modified or substituted with the desired locus from the nonrecurrent parent, while retaining essentially all of the rest of the desired genetic, and therefore the desired physiological and morphological constitution of the original variety. The choice of the particular nonrecurrent parent will depend on the purpose of the backcross; one of the major purposes is to add some commercially desirable trait to the plant. The exact backcrossing protocol will depend on the characteristic or trait being altered and the genetic distance between the recurrent and nonrecurrent parents. Although backcrossing methods are simplified when the characteristic being transferred is a dominant allele, a recessive allele may also be transferred. In this instance it may be necessary to introduce a test of the progeny to determine if the desired characteristic has been successfully transferred.

In one embodiment, progeny bean plants of a backcross in which RS08051272 is the recurrent parent comprise (i) the desired trait from the non-recurrent parent and (ii) all of the physiological and morphological characteristics of bean line RS08051272 as determined at the 5% significance level when grown in the same environmental conditions.

Bean varieties can also be developed from more than two parents. The technique, known as modified backcrossing, uses different recurrent parents during the backcrossing. Modified backcrossing may be used to replace the original recurrent parent with a variety having certain more desirable characteristics or multiple parents may be used to obtain different desirable characteristics from each.

Many single locus traits have been identified that are not regularly selected for in the development of a new inbred but that can be improved by backcrossing techniques. Single locus traits may or may not be transgenic; examples of these traits include, but are not limited to, male sterility, herbicide resistance, resistance to bacterial, fungal, or viral disease, insect resistance, restoration of male fertility, modified fatty acid or carbohydrate metabolism, and enhanced nutritional quality. These comprise genes generally inherited through the nucleus.

Direct selection may be applied where the single locus acts as a dominant trait. An example of a dominant trait is the anthracnose resistance trait. For this selection process, the progeny of the initial cross are sprayed with anthracnose spores prior to the backcrossing. The spraying eliminates any plants which do not have the desired anthracnose resistance characteristic, and only those plants which have the anthracnose resistance gene are used in the subsequent backcross. This process is then repeated for all additional backcross generations.

Selection of bean plants for breeding is not necessarily dependent on the phenotype of a plant and instead can be based on genetic investigations. For example, one can utilize a suitable genetic marker which is closely genetically linked to a trait of interest. One of these markers can be used to identify the presence or absence of a trait in the offspring of a particular cross, and can be used in selection of progeny for continued breeding. This technique is commonly referred to as marker assisted selection. Any other type of genetic marker or other assay which is able to identify the relative presence or absence of a trait of interest in a plant can also be useful for breeding purposes. Procedures for marker assisted selection applicable to the breeding of bean are well known in the art. Such methods will be of particular utility in the case of recessive traits and variable phenotypes, or where conventional assays may be more expensive, time consuming or otherwise disadvantageous. Types of genetic markers which could be used in accordance with the invention include, but are not necessarily limited to, Simple Sequence Length Polymorphisms (SSLPs) (Williams et al., 1990), Randomly Amplified Polymorphic DNAs (RAPDs), DNA Amplification Fingerprinting (DAF), Sequence Characterized Amplified Regions (SCARs), Arbitrary Primed Polymerase Chain Reaction (AP-PCR), Amplified Fragment Length Polymorphisms (AFLPs) (EP 534 858, specifically incorporated herein by reference in its entirety), and Single Nucleotide Polymorphisms (SNPs) (Wang et al., 1998).

F. Plants Derived From Bean Line RS08051272 by Genetic Engineering

Many useful traits that can be introduced by backcrossing, as well as directly into a plant, are those which are introduced by genetic transformation techniques. Genetic transformation may therefore be used to insert a selected transgene into the bean line of the invention or may, alternatively, be used for the preparation of transgenes which can be introduced by backcrossing. Methods for the transformation of plants, including bean, are well known to those of skill in the art. Techniques which may be employed for the genetic transformation of bean include, but are not limited to, electroporation, microprojectile bombardment, *Agrobacterium*-mediated transformation and direct DNA uptake by protoplasts.

As is well known in the art, tissue culture of bean can be used for the in vitro regeneration of a bean plant. Tissue culture of various tissues of beans and regeneration of plants there from is well known. For example, reference may be had to McClean and Grafton (1989); Mergeai and Baudoin (1990); Vanderwesthuizen and Groenewald (1990); Benedicic et al. (1990); Malik and Saxena (1991).

To effect transformation by electroporation, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wound tissues in a controlled manner.

A particularly efficient method for delivering transforming DNA segments to plant cells is microprojectile bombardment. In this method, particles are coated with nucleic acids and delivered into cells by a propelling force. Exemplary particles include those comprised of tungsten, platinum, and preferably, gold. For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate.

An illustrative embodiment of a method for delivering DNA into plant cells by acceleration is the Biolistics Particle Delivery System, which can be used to propel particles coated with DNA or cells through a screen, such as a stainless steel or Nytex screen, onto a surface covered with target bean cells. The screen disperses the particles so that they are not delivered to the recipient cells in large aggregates. It is believed that a screen intervening between the projectile apparatus and the cells to be bombarded reduces the size of projectiles aggregate and may contribute to a higher frequency of transformation by reducing the damage inflicted on the recipient cells by projectiles that are too large.

Microprojectile bombardment techniques are widely applicable, and may be used to transform virtually any plant species. For example, Russell et al. (1993).

*Agrobacterium*-mediated transfer is another widely applicable system for introducing gene loci into plant cells. An advantage of the technique is that DNA can be introduced into whole plant tissues, thereby bypassing the need for regeneration of an intact plant from a protoplast. Modern *Agrobacterium* transformation vectors are capable of replication in *E. coli* as well as *Agrobacterium*, allowing for convenient manipulations (Klee et al., 1985). Moreover, recent technological advances in vectors for *Agrobacterium*-mediated gene transfer have improved the arrangement of genes and restriction sites in the vectors to facilitate the construction of vectors capable of expressing various polypeptide coding genes. The vectors described have convenient multi-linker regions flanked by a promoter and a polyadenylation site for direct expression of inserted polypeptide coding genes. Additionally, *Agrobacterium* containing both armed and disarmed Ti genes can be used for transformation.

In those plant strains where *Agrobacterium*-mediated transformation is efficient, it is the method of choice because of the facile and defined nature of the gene locus transfer. The use of *Agrobacterium*-mediated plant integrating vectors to introduce DNA into plant cells is well known in the art (Fraley et al., 1985; U.S. Pat. No. 5,563,055). *Agrobacterium*-mediated transformation of *P. vulgaris* is described in, for example, Zhang et al. (1997); McClean et al. (1991); Lewis and Bliss (1994); and Song et al. (1995).

Transformation of plant protoplasts also can be achieved using methods based on calcium phosphate precipitation, polyethylene glycol treatment, electroporation, and combinations of these treatments (see, e.g., Potrykus et al., 1985; Omirulleh et al., 1993; Fromm et al., 1986; Uchimiya et al., 1986; Marcotte et al., 1988). Transformation of plants and expression of foreign genetic elements is exemplified in Choi et al. (1994), and Ellul et al. (2003).

A number of promoters have utility for plant gene expression for any gene of interest including but not limited to selectable markers, scoreable markers, genes for pest tolerance, disease resistance, nutritional enhancements and any other gene of agronomic interest. Examples of constitutive promoters useful for garden bean plant gene expression include, but are not limited to, the cauliflower mosaic virus (CaMV) P-35S promoter, which confers constitutive, high-level expression in most plant tissues (see, e.g., Odel et al., 1985), including monocots (see, e.g., Dekeyser et al., 1990; Terada and Shimamoto, 1990); a tandemly duplicated version of the CaMV 35S promoter, the enhanced 35S promoter (P-e35S) the nopaline synthase promoter (An et al., 1988), the octopine synthase promoter (Fromm et al., 1989); and the figwort mosaic virus (P-FMV) promoter as described in U.S. Pat. No. 5,378,619 and an enhanced version of the FMV promoter (P-eFMV) where the promoter sequence of P-FMV is duplicated in tandem, the cauliflower mosaic virus 19S promoter, a sugarcane bacilliform virus promoter, a commelina yellow mottle virus promoter, and other plant DNA virus promoters known to express in plant cells.

With an inducible promoter the rate of transcription increases in response to an inducing agent. Any inducible promoter can be used in the instant invention. A variety of plant gene promoters that are regulated in response to environmental, hormonal, chemical, and/or developmental signals can be used for expression of an operably linked gene in plant cells, including promoters regulated by (1) heat (Callis et al., 1988), (2) light (e.g., pea rbcS-3A promoter, Kuhlemeier et al., 1989; maize rbcS promoter, Schaffner and Sheen, 1991; or chlorophyll a/b-binding protein promoter, Simpson et al., 1985), (3) hormones, such as abscisic acid (Marcotte et al., 1989), (4) wounding (e.g., wun1, Siebertz et al., 1989); or (5) chemicals such as methyl jasmonate, salicylic acid, or Safener. It may also be advantageous to employ organ-specific promoters (e.g., Roshal et al., 1987; Schernthaner et al., 1988; Bustos et al., 1989). Exemplary organ-specific or organ-preferred promoters include, but are not limited to, a root-preferred promoter, such as that from the phaseolin gene (Sengupta-Gopalan et al., 1985); a leaf-specific and light-induced promoter such as that from cab or rubisco (Simpson et al., 1985) and Timko et al., 1985); an anther-specific promoter such as that from LAT52 (Twell et al., 1989); a pollen-specific promoter such as that from Zm13 (Guerrero et al., 1993) or a microspore-preferred promoter such as that from apg (Twell et al, 1993).

Transport of protein produced by transgenes to a subcellular compartment such as the chloroplast, vacuole, peroxisome, glyoxysome, cell wall, or mitochondrion or for secretion into the apoplast, may be accomplished by means of operably linking the nucleotide sequence encoding a signal sequence to the 5' and/or 3' region of a gene encoding the protein of interest. Targeting sequences at the 5' and/or 3' end of the structural gene may determine, during protein synthesis and processing, where the encoded protein is ultimately compartmentalized. The presence of a signal sequence directs a polypeptide to either an intracellular organelle or subcellular compartment or for secretion to the apoplast. Many signal sequences are known in the art. See, for example Becker et al (1992); Knox et al. (1987); Lerner et al. (1989); Fontes et al. (1991); Matsuoka et al. (1991); Gould et al. (1989); Creissen et al. (1991); Kalderon et al. (1984); Steifel et al. (1990).

Exemplary nucleic acids which may be introduced to the bean lines of this invention include, for example, DNA sequences or genes from another species, or even genes or sequences which originate with or are present in the same species, but are incorporated into recipient cells by genetic engineering methods rather than classical reproduction or breeding techniques. However, the term "exogenous" is also intended to refer to genes that are not normally present in the cell being transformed, or perhaps simply not present in the form, structure, etc., as found in the transforming DNA segment or gene, or genes which are normally present and that one desires to express in a manner that differs from the natural expression pattern, e.g., to over-express. Thus, the term "exogenous" gene or DNA is intended to refer to any gene or DNA segment that is introduced into a recipient cell, regardless of whether a similar gene may already be present in such a cell. The type of DNA included in the exogenous DNA can include DNA which is already present in the plant cell, DNA from another plant, DNA from a different organism, or a DNA generated externally, such as a DNA sequence containing an antisense message of a gene, or a DNA sequence encoding a synthetic or modified version of a gene.

Many hundreds if not thousands of different genes are known and could potentially be introduced into a bean plant according to the invention. Non-limiting examples of particular genes and corresponding phenotypes one may choose to introduce into a bean plant include one or more genes for insect tolerance, such as a *Bacillus thuringiensis* (B.t.) gene, pest tolerance such as genes for fungal disease control, herbicide tolerance such as genes conferring glyphosate tolerance, and genes for quality improvements such as yield, nutritional enhancements, environmental or stress tolerances, or any desirable changes in plant physiology, growth, development, morphology or plant product(s). For example, structural genes would include any gene that confers insect tolerance including but not limited to a *Bacillus* insect control protein gene as described in WO 99/31248, herein incorporated by reference in its entirety, U.S. Pat. No. 5,689,052, herein incorporated by reference in its entirety, U.S. Pat. Nos. 5,500,365 and 5,880,275, herein incorporated by reference it their entirety. In another embodiment, the structural gene can confer tolerance to the herbicide glyphosate as conferred by genes including, but not limited to *Agrobacterium* strain CP4 glyphosate resistant EPSPS gene (aroA:CP4) as described in U.S. Pat. No. 5,633,435, herein incorporated by reference in its entirety, or glyphosate oxidoreductase gene (GOX) as described in U.S. Pat. No. 5,463,175, herein incorporated by reference in its entirety.

Alternatively, the DNA coding sequences can affect these phenotypes by encoding a non-translatable RNA molecule that causes the targeted inhibition of expression of an endogenous gene, for example via antisense- or cosuppression-mediated mechanisms (see, for example, Bird et al., 1991). The RNA could also be a catalytic RNA molecule (i.e., a ribozyme) engineered to cleave a desired endogenous mRNA product (see for example, Gibson and Shillito, 1997). Thus, any gene which produces a protein or mRNA which expresses a phenotype or morphology change of interest is useful for the practice of the present invention.

G. Definitions

In the description and tables herein, a number of terms are used. In order to provide a clear and consistent understanding of the specification and claims, the following definitions are provided:

A: When used in conjunction with the word "comprising" or other open language in the claims, the words "a" and "an" denote "one or more."

Allele: Any of one or more alternative forms of a gene locus, all of which alleles relate to one trait or characteristic. In a diploid cell or organism, the two alleles of a given gene occupy corresponding loci on a pair of homologous chromosomes.

Backcrossing: A process in which a breeder repeatedly crosses hybrid progeny, for example a first generation hybrid ($F_1$), back to one of the parents of the hybrid progeny. Backcrossing can be used to introduce one or more single locus conversions from one genetic background into another.

Bean Yield (Tons/Acre): The recovered yield in tons/acre is the yield of the bean pods at harvest versus the means of harvest (hand picked, mechanical harvest).

Broad Adaptation: A cultivar having a broad adaptability means a cultivar or selection that will perform well in different growing conditions, locations, and seasons.

Bush Form: A USDA term about the visual look of the plant. A bean plant is: Spherical (even in width and height), Wide when the bush is wider than tall, High when the bush is taller than wide, or Stem when the individual branches protrude from the shape.

Concentrated set of pods: A concentrated set of pods is said of a plant where a high percentage of all pods on a plant set and mature at the same time so as to facilitate a single harvest.

Crossing: The mating of two parent plants.

Cross-pollination: Fertilization by the union of two gametes from different plants.

Determinate plant: A determinate plant will grow to a fixed number of nodes with a terminal floral raceme on the main stem, while an indeterminate plant continues to grow and never has a terminal floral raceme on the main stem.

Diploid: A cell or organism having two sets of chromosomes.

Dry pod color: The color of dry pods can be Buckskin (a light to pale brown), Salmon (a distinct reddish color), or Green (pale to intense) depending on the expression of the gene for persistent green.

Emasculate: The removal of plant male sex organs or the inactivation of the organs with a cytoplasmic or nuclear genetic factor conferring male sterility or a chemical agent.

Enzymes: Molecules which can act as catalysts in biological reactions. $F_1$ Hybrid: The first generation progeny of the cross of two nonisogenic plants.

Field holding ability: A bean plant that has field holding ability means a plant having pods that remain smooth and retain their color along with a firm fleshy interior as the seed approached physiological maturity.

Genotype: The genetic constitution of a cell or organism.

Haploid: A cell or organism having one set of the two sets of chromosomes in a diploid.

Linkage: A phenomenon wherein alleles on the same chromosome tend to segregate together more often than expected by chance if their transmission was independent.

Machine or mechanical harvest: A machine harvestable plant means a bean plant from which the pods can be removed from the plant one of several commercial mechanical harvesters in such a manner as to reduce broken pods, clusters, and plant matter from the desired pods.

Marker: A readily detectable phenotype, preferably inherited in codominant fashion (both alleles at a locus in a diploid heterozygote are readily detectable), with no environmental variance component, i.e., heritability of 1.

Maturity: A maturity under 53 days is considered early while one between 54-59 days would be considered average or medium and one of 60 or more days would be late.

Maturity Date: Plants are considered mature when the pods have reached their maximum desirable seed size and sieve size for the specific use intended. This can vary for each end user, e.g., processing at different stages of maturity would be required for different types of consumer beans such as "whole pack," "cut" or "French style." The number of days is calculated from a relative planting date which depends on day length, heat units and other environmental factors.

Phenotype: The detectable characteristics of a cell or organism, which characteristics are the manifestation of gene expression.

Pod Color: A USDA term where light green color is defined by the variety Provider and a dark green color by the variety Bush Blue Lake 290. Yellow is defined as color of the wax bean Goldrush.

Pod Position: The pod position is the location of the pods within the plant. The pods can be high (near the top), low (near the bottom), or medium (in the middle) of the plant, or scattered throughout the plant.

Quantitative Trait Loci (QTL): Quantitative trait loci (QTL) refer to genetic loci that control to some degree numerically representable traits that are usually continuously distributed.

Regeneration: The development of a plant from tissue culture.

Seed development: The rate at which seeds develop as pods reach their harvest diameter. A slow seed development characteristic will give a cultivar its field holding ability, and a larger harvest window.

Self-pollination: The transfer of pollen from the anther to the stigma of the same plant.

Single Locus Converted (Conversion) Plant: Plants which are developed by a plant breeding technique called backcrossing, wherein essentially all of the desired morphological and physiological characteristics of a garden bean variety are recovered in addition to the characteristics of the single locus transferred into the variety via the backcrossing technique and/or by genetic transformation.

Substantially Equivalent: A characteristic that, when compared, does not show a statistically significant difference (e.g., p=0.05) from the mean.

Tetraploid: A cell or organism having four sets of chromosomes.

Tissue Culture: A composition comprising isolated cells of the same or a different type or a collection of such cells organized into parts of a plant.

Transgene: A genetic locus comprising a sequence which has been introduced into the genome of a garden bean plant by transformation.

Triploid: A cell or organism having three sets of chromosomes.

H. Deposit Information

A deposit of bean line RS08051272, disclosed above and recited in the claims, has been made with the American Type Culture Collection (ATCC), 10801 University Blvd., Manassas, Va. 20110-2209. The date of deposit was Mar. 3, 2008. Upon issuance of a patent, all restrictions upon the deposit will be removed, and the deposit is intended to meet all of the requirements of 37 C.F.R. §1.801-1.809. The accession number for those deposited seeds of bean line RS08051272 is ATCC Accession No. PTA-8987. The deposit will be maintained in the depository for a period of 30 years, or 5 years after the last request, or for the effective life of the patent, whichever is longer, and will be replaced if necessary during that period.

Although the foregoing invention has been described in some detail by way of illustration and example for purposes of clarity and understanding, it will be obvious that certain changes and modifications may be practiced within the scope of the invention, as limited only by the scope of the appended claims.

All references cited herein are hereby expressly incorporated herein by reference.

REFERENCES

The following references, to the extent that they provide exemplary procedural or other details supplementary to those set forth herein, are specifically incorporated herein by reference:

U.S. Pat. No. 5,463,175
U.S. Pat. No. 5,500,365
U.S. Pat. No. 5,563,055
U.S. Pat. No. 5,633,435
U.S. Pat. No. 5,689,052
U.S. Pat. No. 5,880,275
U.S. Pat. No. 5,378,619
An et al., *Plant Physiol.*, 88:547, 1988.
Becker et al., *Plant Mol. Biol.*, 20:49, 1992.
Benedicic et al., *Plant Cell Tissue Org. Cult.*, 24:199-206, 1990.
Bird et al., *Biotech. Gen. Engin. Rev.*, 9:207, 1991.
Bustos et al., *Plant Cell*, 1:839, 1989.
Callis et al., *Plant Physiol.*, 88:965, 1988.
Choi et al, *Plant Cell Rep.*, 13: 344-348, 1994.
Creissen et al, *Plant J.*, 2:129, 1991.
Dekeyser et al., *Plant Cell*, 2:591, 1990.
Ellul et al., *Theor. Appl. Genet.*, 107:462-469, 2003.
EP 534 858
Fontes et al., *Plant Cell*, 3:483-496, 1991.
Fraley et al., *Bio/Technology*, 3:629-635, 1985.
Fromm et al., *Nature*, 312:791-793, 1986.
Fromm et al., *Plant Cell*, 1:977, 1989.
Gibson and Shillito, *Mol. Biotech.*, 7:125, 1997
Gould et al., *J. Cell. Biol.*, 108:1657, 1989.
Guerrero et al., *Mol. Gen. Genetics*, 244:161-168, 1993.
Kalderon et al., *Cell*, 39:499-509, 1984.
Klee et al., *Bio-Technology*, 3(7):637-642, 1985.
Knox et al., *Plant Mol. Biol.*, 9:3-17, 1987.
Kuhlemeier et al., *Plant Cell*, 1:471, 1989.
Lerner et al, *Plant Physiol.*, 91:124-129, 1989.

Lewis and Bliss, *J. American Soc. Horticul. Sci.,* 119:361-366, 1994.
Malik, and Saxena, *Planta,* 184(1):148-150, 1991.
Marcotte et al., *Nature,* 335:454, 1988.
Marcotte et al., *Plant Cell,* 1:969, 1989.
Matsuoka et al, *Proc. Natl. Acad. Sci. USA,* 88:834, 1991.
McClean and Grafton, *Plant Sci.,* 60:117-122, 1989.
McClean et al, *Plant Cell Tiss. Org. Cult.,* 24:131-138, 1991.
Mergeai and Baudoin, *B. I. C. Invit. Papers,* 33:115-116, 1990.
Odel et al, *Nature,* 313:810, 1985.
Omirulleh et al., *Plant Mol. Biol.,* 21(3):415-428, 1993.
Potrykus et al., *Mol. Gen. Genet.,* 199:183-188, 1985.
Roshal et al., *EMBO J.,* 6:1155, 1987.
Russell et al., *Plant Cell Reports,* 12(3):165-169 (1993.
Schaffner and Sheen, *Plant Cell,* 3:997, 1991.
Schernthaner et al., *EMBO J.,* 7:1249, 1988.
Sengupta-Gopalan et al., *Proc. Natl. Acad. Sci. USA,* 82:3320-3324, 1985.
Siebertz et al., *Plant Cell,* 1:961, 1989.
Simpson et al., *EMBO J.,* 4:2723, 1985.
Song et al., *J. Plant Physiol,* 146:148-154, 1995.
Steifel et al., *Plant Cell,* 2:785-793, 1990.
Terada and Shimamoto, *Mol. Gen. Genet.,* 220:389, 1990.
Timko et al., *Nature,* 318:579-582, 1985.
Twell et al., *Mol. Gen. Genetics,* 217:240-245, 1989.
Twell et al., *Sex. Plant Reprod.,* 6:217-224, 1993.
Uchimiya et al., *Mol. Gen. Genet.,* 204:204, 1986.
Vanderwesthuizen and Groenewald, *S. Afr. J. Bot.,* 56:271-273, 1990.
Wang et al, *Science,* 280:1077-1082, 1998.
Williams et al., *Nucleic Acids Res.,* 1 8:6531-6535, 1990.
WO 99/31248
Zhang et al., *J. American Soc. Horticul. Sci.,* 122(3):300-305, 1997.

What is claimed is:

1. A seed of bean line RS08051272, a sample of seed of said line having been deposited under ATCC Accession Number PTA-8987.

2. A plant of bean line RS08051272, a sample of seed of said line having been deposited under ATCC Accession Number PTA-8987.

3. A plant part of the plant of claim 2.

4. The plant part of claim 3, wherein said part is selected from the group consisting of a pod, pollen, an ovule and a cell.

5. A bean plant, or a part thereof, having all the physiological and morphological characteristics of the bean plant of claim 2.

6. A tissue culture of regenerable cells of bean line RS08051272, a sample of seed of said line having been deposited under ATCC Accession Number PTA-8987.

7. The tissue culture according to claim 6, comprising cells or protoplasts from a plant part selected from the group consisting of embryos, meristems, cotyledons, pollen, leaves, anthers, roots, root tips, pistil, flower, seed and stalks.

8. A bean plant regenerated from the tissue culture of claim 6, wherein the regenerated plant expresses all of the physiological and morphological characteristics of bean line RS08051272, a sample of seed of said line having been deposited under ATCC Accession Number PTA-8987.

9. A method of producing bean seed, comprising crossing the plant of claim 2 with itself or a second bean plant.

10. The method of claim 9, wherein the plant of bean line RS08051272 is the female parent.

11. The method of claim 9, wherein the plant of bean line RS08051272 is the male parent.

12. An F1 hybrid seed produced by the method of claim 9.

13. An F1 hybrid plant produced by growing the seed of claim 12.

14. A method for producing a seed of a line RS08051272-derived bean plant comprising the steps of:
(a) crossing a bean plant of line RS08051272 with a second bean plant, a sample of seed of said line having been deposited under ATCC Accession Number PTA-8987; and
(b) allowing seed of a RS08051272-derived bean plant to form.

15. The method of claim 14, further comprising the steps of:
(c) crossing a plant grown from said RS08051272-derived bean seed with itself or a second bean plant to yield additional RS08051272-derived bean seed;
(d) growing said additional RS08051272-derived bean seed of step (c) to yield additional RS08051272-derived bean plants; and
(e) repeating the crossing and growing steps of (c) and (d) to generate further RS08051272-derived bean plants.

16. A method of vegetatively propagating a plant of bean line RS08051272 comprising the steps of:
(a) collecting tissue capable of being propagated from a plant of bean line RS08051272, a sample of seed of said line having been deposited under ATCC Accession Number PTA-8987;
(b) cultivating said tissue to obtain proliferated shoots; and
(c) rooting said proliferated shoots to obtain rooted plantlets.

17. The method of claim 16, further comprising growing plants from said rooted plantlets.

18. A method of introducing a desired trait into bean line RS08051272 comprising:
(a) crossing a plant of line RS08051272 with a second bean plant that comprises a desired trait to produce F1 progeny, a sample of seed of said line RS08051272 having been deposited under ATCC Accession Number PTA-8987;
(b) selecting an F1 progeny that comprises the desired trait;
(c) crossing the selected F1 progeny with a plant of line RS08051272 to produce backcross progeny;
(d) selecting backcross progeny comprising the desired trait and the physiological and morphological characteristic of bean line RS08051272; and
(e) repeating steps (c) and (d) three or more times in succession to produce selected fourth or higher backcross progeny that comprise the desired trait and all of the physiological and morphological characteristics of bean line RS08051272 when grown in the same environmental conditions.

19. A bean plant produced by the method of claim 18.

20. A method of producing a plant of bean line RS08051272 comprising an added desired trait, the method comprising introducing a transgene conferring the desired trait into a plant of bean line RS08051272, a sample of seed of said line RS08051272 having been deposited under ATCC Accession Number PTA-8987.

21. A progeny plant of the plant of claim 2 that comprises all of the physiological and morphological characteristics of bean line RS08051272, a sample of seed of said line having been deposited under ATCC Accession Number PTA-8987.

22. A seed that produces the plant of claim 21.

23. A method of producing beans comprising:
(a) obtaining the plant of claim 2, wherein the plant has been cultivated to maturity, and
(b) collecting beans from the plant.

* * * * *